(12) United States Patent
Ban et al.

(10) Patent No.: US 7,312,069 B2
(45) Date of Patent: Dec. 25, 2007

(54) METHOD OF ANALYZING LIGAND IN SAMPLE AND APPARATUS FOR ANALYZING LIGAND IN SAMPLE

(75) Inventors: Tomoaki Ban, Toon (JP); Hideki Kirino, Toon (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/570,654

(22) PCT Filed: Dec. 22, 2004

(86) PCT No.: PCT/JP2004/019177

§ 371 (c)(1),
(2), (4) Date: Mar. 3, 2006

(87) PCT Pub. No.: WO2005/064317

PCT Pub. Date: Jul. 14, 2005

(65) Prior Publication Data

US 2007/0031891 A1 Feb. 8, 2007

(30) Foreign Application Priority Data

Dec. 26, 2003 (JP) ............................. 2003-433162

(51) Int. Cl.
*G01N 33/553* (2006.01)
(52) U.S. Cl. .................. 435/287.2; 385/129; 385/130; 422/57; 422/82.05; 422/82.11; 435/6; 435/287.1; 435/288.7; 435/808; 436/164; 436/165; 436/518; 436/524; 436/525; 436/805; 436/817
(58) Field of Classification Search ................ None
See application file for complete search history.

(56) References Cited

U.S. PATENT DOCUMENTS

| | | | | |
|---|---|---|---|---|
| 6,161,437 A | * | 12/2000 | Brennan et al. ............... | 73/655 |
| 6,649,361 B1 | | 11/2003 | Iwasaki et al. | |
| 2002/0001085 A1 | | 1/2002 | Dickopf et al. | |

FOREIGN PATENT DOCUMENTS

| | | |
|---|---|---|
| JP | 2001-194298 | 7/2001 |
| JP | 2002-530668 | 9/2002 |
| JP | 2003-65947 | 3/2003 |
| JP | 2003-66004 | 3/2003 |
| JP | 2003-75336 | 3/2003 |

OTHER PUBLICATIONS

Sota, et al., "Detection of Conformational Changes in an Immobilized Protein Using Surface Plasmon Resonance", Anal. Chem., 1998, vol. 70, pp. 2019-2024.

* cited by examiner

Primary Examiner—Christopher L. Chin
(74) Attorney, Agent, or Firm—Hamre, Schumann, Mueller & Larson, P.C.

(57) ABSTRACT

A sample analyzing method capable of high-precision analysis without being affected by vibration and optical design is provided. In the sample analyzing method, a sample containing a ligand is caused to bind to a receptor that can bind specifically to the ligand, and a change caused by binding of the receptor and the ligand is analyzed by measuring frequency characteristics of a surface plasmon resonance angle while applying external vibration to the receptor. The sample analyzing method is useful in the fields of, for example, biology, medicine, pharmacology, agriculture, and the like.

16 Claims, 8 Drawing Sheets

(Inside ligand) (Between ligands) (Electrode)

METHOD OF ANALYZING LIGAND IN SAMPLE AND APPARATUS FOR ANALYZING LIGAND IN SAMPLE

TECHNICAL FIELD

The present invention relates to a method for analyzing a ligand in a sample and an apparatus for analyzing a ligand in a sample.

BACKGROUND ART

Among biochemical reactions, the reaction of binding a receptor and a ligand is important. For example, in an antigen-antibody reaction, an antibody as a receptor binds to an antigen as a ligand. For example, in an enzymatic reaction, an enzyme as a receptor binds to an enzyme substrate as a ligand. By utilizing these reactions, a ligand present in a sample can be detected.

For example, a receptor is bound to a metal thin film surface. When a ligand binds to the receptor, the dielectric constant in the vicinity of the metal thin film is changed. A method of using a surface plasmon resonance phenomenon to detect such a change and thereby analyze the amount of a receptor-ligand complex, has been known (see, for example, Non-patent document 1). In this method, initially, a metal thin film to whose surface a receptor is bound as described above is irradiated from the rear side with light at an angle that satisfies a total internal reflection condition. When the angle is a specific incident angle that causes the wave number of a surface plasmon excited by the incident light to be equal to the wave number of an evanescent wave derived from the excitation light, a portion of the amount of the incident light is used for excitation of the surface plasmon, so that the amount of reflected light is reduced. For example, in order to detect the dielectric constant change in the vicinity of the metal thin film, a method of measuring reflected light while changing the angle of incident light to determine an angle of incident light at which absorption is highest, and a method of determining an angle of reflected light at which absorption is highest where the angle of incident light is held constant, have been known. In addition, a technique of applying an electric field (electrical vibration) to the rear side of a metal thin film on which a receptor is immobilized to control separation and movement of a sample on the metal thin film (see, for example, Patent document 1) and a technique of using a change in refractive index of a metal thin film to measure a large amount of sample at a time (see, for example, Patent document 2), have been proposed.

However, in these methods, the amount of a ligand binding to a receptor is analyzed based on a minute amount of angle change corresponding to a reduction in light amount due to excitation of surface plasmon. Therefore, in these methods, the surface of a metal thin film (e.g., thickness: about several nanometers) on which incident light is reflected needs to be even. In addition, since a minute angle change amount is measured based on a change in light amount, optical parts need to be adjusted with high precision so that light can be received without deviation of an optical axis. As a result, apparatuses for use in these methods tend to be influenced by optical design. In addition, since a minute change is detected, reading precision deteriorates significantly when an apparatus suffers from vibration during measurement. Therefore, it is difficult to produce portable apparatuses that are suitable for these methods.

Non-patent document 1: Anal. Chem., 1998, 70,2019-2024

Patent document 1: JP 2003-65947 A
Patent document 2: JP 2003-75336 A

DISCLOSURE OF INVENTION

Problem to be Solved by the Invention

An object of the present invention is to provide a method and an apparatus for analyzing a ligand in a sample with high precision that are less susceptible to vibration and optical design compared with conventional techniques.

Means for Solving Problem

In order to achieve the object, the present invention provides a method for analyzing a ligand in a sample, comprising the steps of providing a sample containing a ligand, providing a metal thin film, wherein a receptor that can bind specifically to a ligand is immobilized on one side of the metal thin film, an optical prism is provided on an opposite side of the metal thin film, and the metal thin film can cause surface plasmon resonance, providing irradiating means for irradiating with measuring light, providing light receiving means for receiving reflected light of the measuring light, providing analyzing means for analyzing a ligand binding to the receptor, causing the sample and the metal thin film to contact each other so that the ligand in the sample binds to the receptor, irradiating the side of the metal thin film opposite to the side on which the receptor is immobilized with measuring light using the irradiating means, receiving reflected light of the measuring light reflected on the side of the metal thin film using the light receiving means, and detecting a change in a surface plasmon resonance angle caused by a change in a dielectric constant of a vicinity of the metal thin film, based on the reflected light, using the analyzing means, further comprising providing applying means for applying external vibration to a region in which the receptor is immobilized, applying external vibration to the side of the metal thin film on which the receptor is immobilized, using the applying means, while irradiating the metal thin film with the measuring light using the irradiating means, and obtaining frequency characteristics of a surface plasmon resonance angle with respect to external vibration using the analyzing means, and based on the frequency characteristics, analyzing a ligand in the sample binding to the receptor.

The present invention also provides an apparatus for analyzing a ligand in a sample, comprising a metal thin film, wherein a receptor that can bind specifically to a ligand is immobilized on one side of the metal thin film, an optical prism is provided on an opposite side of the metal thin film, and the metal thin film can cause surface plasmon resonance, irradiating means for irradiating with measuring light, light receiving means for receiving reflected light of the measuring light reflected on the side of the metal thin film, and analyzing means for analyzing a ligand binding to the receptor, and further applying means for applying external vibration to the side of the metal thin film on which the receptor is immobilized. A side of the metal thin film opposite to the side on which the receptor is immobilized can be irradiated with measuring light using the irradiating means while applying external vibration using the applying means, and the analyzing means can detect a change in a surface plasmon resonance angle from the reflected light and obtain frequency characteristics of a surface plasmon resonance angle with respect to external vibration, and based on the frequency characteristics, analyze a ligand in the sample binding to the receptor.

Effects of the Invention

As described above, in the analyzing method and apparatus of the present invention, external vibration is applied, and the frequency characteristics of a surface plasmon resonance angle with respect to the external vibration are obtained. Due to the external vibration, a dielectric constant in a vicinity of the metal thin film is changed. The dielectric constant change causes a change in the surface plasmon resonance angle. Thus, the analyzing method and apparatus of the present invention measures the frequency characteristics of the surface plasmon resonance angle. Therefore, it is not necessary to measure a minute change in the surface plasmon resonance angle. As a result, it is possible to achieve high-precision analysis without being affected significantly by vibration and optical design. In addition, the apparatus of the present invention can resist vibration, and therefore, can be miniaturized.

BRIEF DESCRIPTION OF THE DRAWINGS

FIG. 2 is a diagram for explaining a method for evaluating a physical property by applying electrical vibration as external vibration, in an exemplary apparatus of the present invention.

FIG. 3 illustrates examples of a surface plasmon resonance curve measured when no receptor was provided on a metal thin film, and a surface plasmon resonance curve measured when water was provided as a receptor, in an exemplary apparatus of the present invention.

FIG. 4A(a) illustrates a surface plasmon resonance curve in the absence of a ligand, and FIG. 4A(b) is a partially enlarged view of FIG. 4A(a).

FIG. 4B(a) illustrates a surface plasmon resonance curve when albumin bovine serum was used as a ligand, and FIG. 4B(b) illustrates a partially enlarged view of FIG. 4B(a).

FIG. 5 illustrates a schematic diagram indicating exemplary states of a vicinity of a metal thin film depending on the intensity of external vibration, in the apparatus of the present invention.

FIG. 6 illustrates a diagram for explaining a relationship between external vibration and binding of a receptor and a ligand in the present invention.

DESCRIPTION OF THE INVENTION

Figure 1:
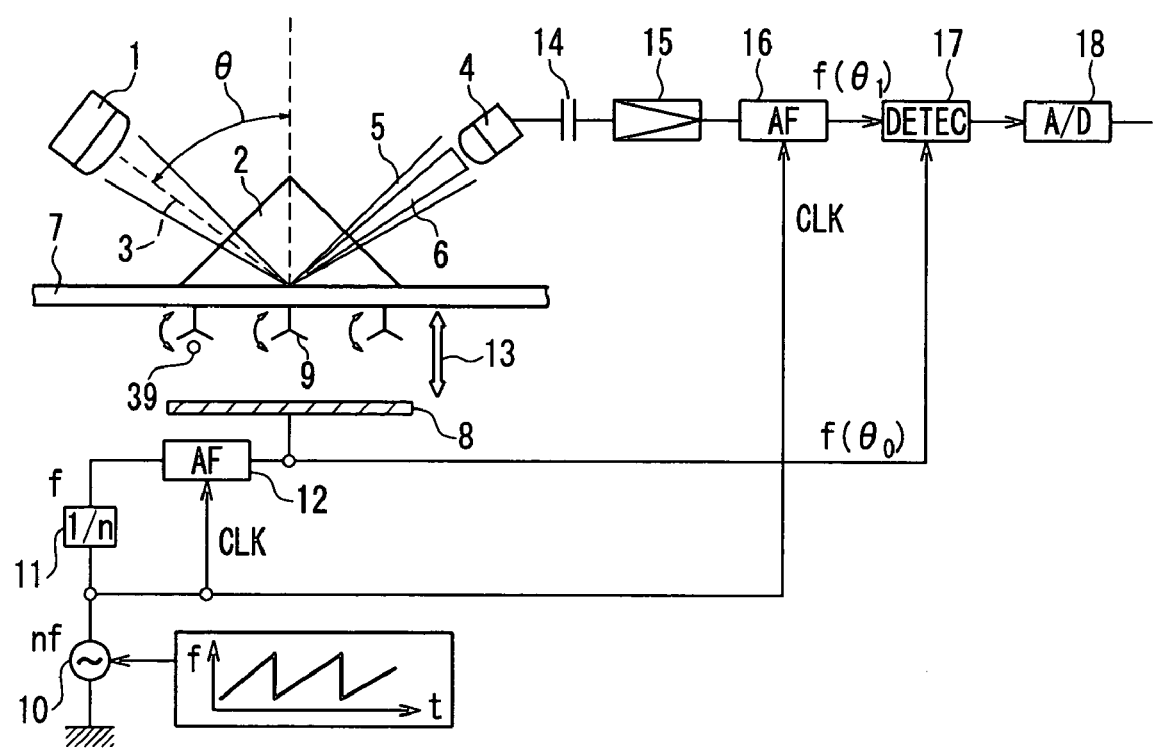
FIG. 1 is a schematic diagram illustrating an exemplary apparatus of the present invention.

In the analyzing method and apparatus of the present invention, at least one of a receptor and a ligand preferably is charged. This is because, in this case, the dielectric constant of the metal thin film surface can be easily changed when electrical vibration is applied as external vibration. Examples of a combination of a receptor and a ligand include an antigen and an antibody; an antibody and an antigen; a hormone and a hormone receptor; a hormone receptor and a hormone; a polynucleotide and a polynucleotide receptor; a polynucleotide receptor and a polynucleotide; an enzyme inhibitor and an enzyme; an enzyme and an enzyme inhibitor; an enzyme substrate and an enzyme; an enzyme and an enzyme substrate; and the like.

The present inventors infer a mechanism of the dielectric constant change in the vicinity of the metal thin film as follows. When external vibration is applied to the receptor and the ligand, the receptor and the ligand follow the metal thin film and gather close together on the metal thin film surface. As a result, the molecular density of an evanescent region on the metal thin film is changed. The molecular density change is responsible for a change in the dielectric constant of the evanescent region, i.e., the dielectric constant change in the vicinity of the metal thin film.

In the analyzing method of the present invention, the applying means preferably is means for applying at least one of electrical vibration, magnetic vibration, and mechanical vibration, more preferably, means for applying at least electrical vibration. In this case, the applying means is means for applying at least electrical vibration, and the analyzing means preferably further includes analyzing a physical property of the ligand from the reflected light. This is because, in this case, the physical property of the ligand can be easily analyzed. Similarly, in the apparatus of the present invention, the applying means preferably is means for applying at least one of electrical vibration, magnetic vibration, and mechanical vibration, more preferably means for applying at least electrical vibration. In this case, the applying means is means for applying at least electrical vibration, and the analyzing means preferably can analyze a physical property of the ligand from the reflected light. This is because, in this case, the physical property of the ligand, the analysis of which conventionally requires another apparatus, can be analyzed simultaneously. The electrical vibration further preferably is provided by using an alternating current electric field. This is because, by applying alternating current electric field, an electrochemical property, such as a charge number, an electrical resistance value, or the like, of at least one of the ligand and the receptor can be evaluated simultaneously.

In the analyzing method of the present invention, an amount of a ligand in the sample binding to the receptor preferably is analyzed. Similarly, in the apparatus of the present invention, an amount of a ligand in the sample binding to the receptor preferably is analyzed.

In the analyzing method of the present invention, preferably, the analyzing means further comprises comparing means for comparing a phase of the external vibration with a phase of a signal component of the external vibration included in the reflected light, and the step of obtaining the frequency characteristics uses the comparing means to compare the phase of the external vibration with the phase of the signal component of the external vibration included in the reflected light, to detect a point of inflection (following frequency limit) of the frequency characteristics. This is because, by detecting the point of inflection of the frequency characteristics, a result having higher measurement precision can be obtained than that of a method of measuring a change in a surface plasmon resonance angle. Similarly, in the apparatus of the present invention, the analyzing means further comprises comparing means capable of comparing a phase of the external vibration with a phase of a signal component of the external vibration included in the reflected light, to detect a point of inflection (following frequency limit) of the frequency characteristics. This is because, by detecting the point of inflection of the frequency characteristics, a result having higher measurement precision can be obtained than when a change in a surface plasmon resonance angle is measured.

Preferably, the analyzing method of the present invention further comprises providing measuring means for measuring a temporal change in the point of inflection of the frequency characteristics, and by measuring the temporal change in the point of inflection of the frequency characteristics using the measuring means, the degree of binding of the receptor and the ligand is detected. This is because, in this case, the degree of the progress of binding of the receptor and the ligand can be measured. Similarly, it is preferable that in the apparatus of the present invention, measuring means is further included, and by measuring a temporal change in the point of inflection of the frequency characteristics using the measuring means, the degree of binding of the receptor and the ligand can be detected. This is because, in this case, the degree of the progress of binding of the receptor and the ligand can be measured.

Preferably, the analyzing method of the present invention further comprises providing optical means for causing reflected light of the measuring light reflected on the side of the metal thin film on which the receptor is immobilized to impinge on the side further a plurality of times, and the optical means is used to cause reflected light of the measuring light reflected on the side of the metal thin film on which the receptor is immobilized, to impinge on the side further a plurality of times, and the reflected light of the measuring light received by the light receiving means is the reflected light of the measuring light reflected a plurality of times on the side of the metal thin film using the optical means. This is because, in this case, a plurality of times of reflection amplifies the amplitude of the surface plasmon resonance angle to achieve high-sensitivity measurement. Similarly, it is preferable that the apparatus of the present invention further comprises optical means capable of causing the reflected light of the measuring light reflected on the side of the metal thin film on which the receptor is immobilized, to impinge on the side further a plurality of times, and the reflected light of the measuring light received by the light receiving means is the reflected light of the measuring light reflected a plurality of times on the side of the metal thin film using the optical means. This is because, in this case, a plurality of times of reflection amplifies the amplitude of the surface plasmon resonance angle to achieve high-sensitivity measurement.

First Embodiment

In a first embodiment of the present invention, a preferable embodiment of the apparatus of the present invention will be described. FIG. 1 is a schematic diagram illustrating an example of the apparatus of the present invention. In FIG. 1, 1 indicates a light source, 2 indicates a prism, 3 indicates measuring light. 4 indicates a light receiving apparatus. 5 indicates reflected light. 6 indicates a reflected light dark portion in which the amount of light is partially reduced due to excitation of plasmon. 7 indicates a metal thin film and upper electrode. 8 indicates a lower electrode. 9 indicates a receptor immobilized on the metal film and upper electrode 7. 10 indicates an alternating current source. 11 indicates a frequency divider that divides a frequency of the alternating current source 10. 12 and 16 each indicate an active filter that passes only a specific frequency. 13 indicates external vibration. 14 indicates a capacitor. 15 indicates an amplifier. 17 indicates a detector that compares a phase ($\theta_0$) of external vibration with a phase ($\theta_1$) of a signal component of external vibration included in reflected light. 18 indicates an A/D converter that converts an analog signal obtained by the detector 17 into a digital signal. 39 indicates a ligand, and $\theta$ indicates an incident angle.

The light source 1 is provided at a location that allows the measuring light 3 emitted by the light source 1 to impinge on the metal thin film and upper electrode 7. The receptor 9 is immobilized on a side opposite to an irradiated side of the metal thin film and upper electrode 7 that is irradiated. The light receiving apparatus 4 is provided at a location that allows the light receiving apparatus 4 to receive the reflected light 5 from the metal thin film and upper electrode 7. The lower electrode 8 is disposed so that external vibration can be applied to the receptor 9 immobilized on the metal thin film and upper electrode 7. The lower electrode 8 is connected via the frequency divider 11 and the active filter 12 to the alternating current source 10, and the alternating current source 10 also is connected to the other active filter 16. The active filter 16 is connected via the capacitor 14 and the amplifier 15 in this order to the light receiving apparatus 4. Both the active filter 16 and the active filter 12 are connected via the detector 17 to the A/D converter 18. In FIG. 1, the metal thin film and upper electrode 7 is provided in an upper portion of the apparatus, while the lower electrode 8 is provided in a lower portion of the apparatus. Alternatively, the positional upper-lower relationship may be reversed, or the electrodes may be provided effectively on right and left sides of the apparatus.

The measuring light 3 emitted by the light source 1 is passed through a beam splitter (not shown) to extract p-polarized light, and only the p-polarized light is passed through the prism 2 (e.g., a prism manufactured by Nippon Denshi Reza) while changing the incident angle $\theta$ and is brought onto the metal thin film and upper electrode 7. The measuring light 3 incident to the metal thin film and upper electrode 7 is reflected totally on the metal thin film and upper electrode 7 to generate the reflected light 5. When the measuring light 3 is caused to enter the metal thin film and upper electrode 7 at a certain particular incident angle $\theta$, on evanescent wave is generated, so that a portion of the light amount is used for excitation of plasmon wave that is called surface plasmon resonance, and a reflected light dark portion 6 having a reduced light amount is generated. The light receiving apparatus 4 that converts an intensity of the reflected light 5 into a voltage is used to detect the intensity of the reflected light 5 including the reflected light dark portion 6.

Further, a unit composed of the alternating current source 10 and the frequency divider 11 is connected to the metal thin film and upper electrode 7 and the lower electrode 8.

The alternating current source 10 generates a frequency of nf, which is in turn converted into a frequency of f by the frequency divider 11. The lower electrode 8 applies the external vibration 13 having a frequency of f to the metal thin film and upper electrode 7. As a result, the receptor 9 is vibrated due to a change in direction of the molecule. The electronic polarization component of the receptor molecule is dominantly responsible for the dielectric constant of an evanescent wave region with respect to the measuring light. When a direction of the receptor 9 in an evanescent region of the surface of the metal thin film and upper electrode 7 is changed due to the external vibration 13, a center of electron density also is changed, so that the dielectric constant is changed, and the particular angle of the reflected light dark portion 6 at which plasmon resonance is generated is changed within a range including the light receiving apparatus 4.

When the ligand 39 binds to the receptor 9 in the vicinity of the metal thin film and upper electrode 7, the weight of the receptor 9 is increased by the molecular weight of the ligand 39. As a result, the dielectric constant of a complex of the receptor 9 and the ligand 39 is changed from the dielectric constant of only the receptor 9. When the external vibration 13 is applied to the receptor 9 to which the ligand 39 binds, the frequency characteristics of vibration are changed due to the direction change of the receptor 9 with respect to the external vibration 13.

The reflected light 5 including the reflected light dark portion 6 is detected by the light receiving apparatus 4, and the alternating current component is passed through and amplified by the amplifier 15. The active filter 16 removes components other than a signal component of external vibration. The detector 17 compares the phase ($\theta_0$) of external vibration with the phase ($\theta_1$) of a signal component of external vibration included in reflected light. The obtained analog signal is converted into a digital signal by the A/D converter 18.

In the apparatus of the present invention, by measuring the frequency characteristics of the surface plasmon resonance angle, it is possible to analyze a ligand binding to a receptor, for example, it is possible to analyze an amount of a ligand binding to a receptor. Thus, in the apparatus of the present invention, it is not necessary to read a minute change in angle of the reflected light dark portion 6, whereby the optical flatness of a measuring instrument, such as the prism 2, the metal thin film and upper electrode 7, or the like, is relaxed. Further, in the apparatus of the present invention, the light receiving apparatus 4 may be provided at a location within a change range of the reflected light dark portion 6, so that the influence of noise is reduced, thereby making it possible to achieve high-sensitivity measurement.

Figure 2A:
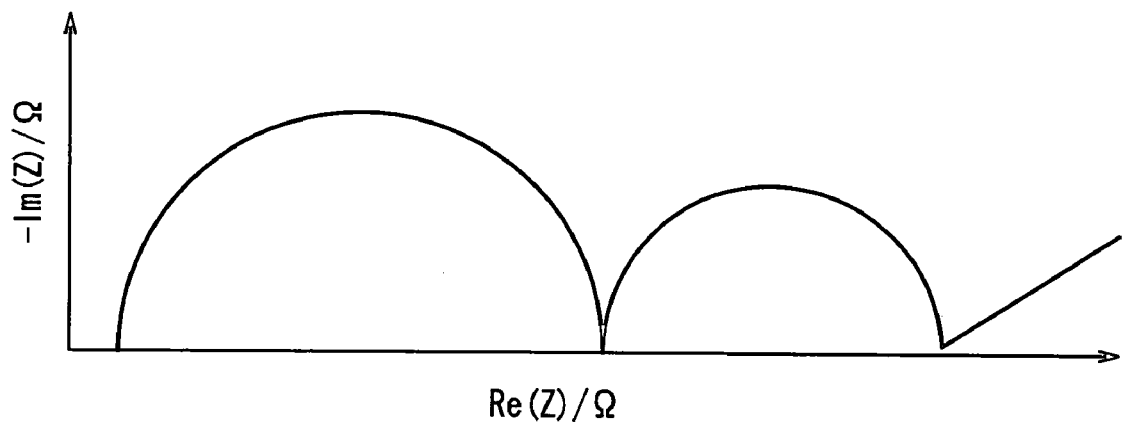
FIG. 2(a) is a diagram illustrating frequency characteristics of an impedance of a ligand that were measured.
Figure 2B:
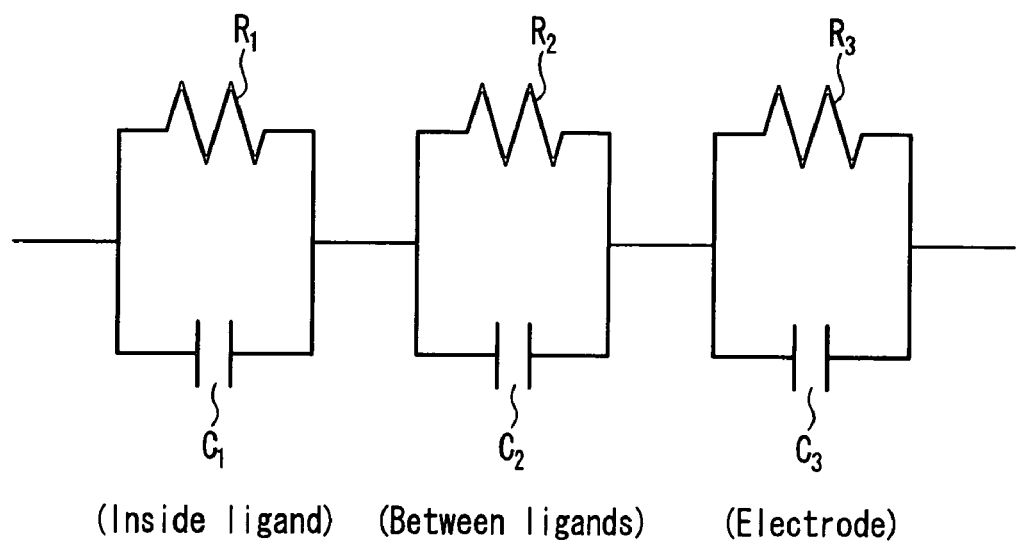
FIG. 2(b) is a schematic diagram in which a ligand is represented by a combination of equivalent circuits.

Since the optical flatness of a measuring instrument, the precision of parts, and the precision of an optical axis are relaxed, the apparatus of the present invention can be manufactured with low cost and can be provided as a portable and small-size apparatus that resists vibration. Further, by applying electrical vibration as external vibration, a physical property of a ligand that conventionally cannot be evaluated simultaneously, such as a charge number, an electrical resistance value, or the like, can be evaluated. For example, a predetermined voltage is applied between the metal thin film and upper electrode 7 and the lower electrode 8 while changing a frequency generated from the alternating current source 10, and by measuring a current flowing at that time, frequency characteristics of impedance is obtained as illustrated in FIG. 2(*a*). A ligand contained in a sample can be represented by a combination of equivalent circuits, such as a resistance (R), a capacitance (C), and the like, as illustrated in FIG. 2(*b*). Impedance Z is Z=R+jX in the case of series arrangement, and $Z=RX^2/(R^2+X^2)+jR^2X/(R^2+X^2)$ in the case of parallel arrangement (in the expressions, $X=-1/(2\pi fC)$). For example, these expressions are applied to the impedance-frequency characteristics of FIG. 2(*a*) for analysis, thereby making it possible to evaluate each property. Note that the method of applying a predetermined voltage between the metal thin film and upper electrode 7 and the lower electrode 8 while changing a frequency generated by the alternating current source 10, and analyzing a current flowing at that time has been described. This method may be achieved by applying a predetermined voltage between the metal thin film and upper electrode 7 and the lower electrode 8 while changing a frequency generated by the alternating current source 10, and measuring a voltage applied at that time. Note that, in FIG. 2(*b*), $R_1$, $R_2$, and $R_3$ indicate a resistance in a ligand, a resistance between ligands, and a resistance of an electrode, respectively, and $C_1$, $C_2$, and $C_3$ indicate a capacitance in a ligand, a capacitance between ligands, and a capacitance of an electrode, respectively.

Note that, as the light source 1, an He—Ne laser, an Ar laser, a pigment laser, or the like can be used. For example, the light source 1 may be composed of an AlGaAs double heterojunction visible light semiconductor laser (e.g., manufactured by ROHM Co., Ltd.), a collimating lens (for example, Panasonic Electronic Devices Nitto Co., Ltd.), and a polarized beam splitter (for example, manufactured by Sigma Koki Co., Ltd.). As a method for changing the incident angle, the light source 1 may be driven to move the measuring light 3 to scan the metal thin film and upper electrode 7, or alternatively, the light source 1 is fixed and a reflection mirror, such as a polygon mirror scanner or the like, is driven to move the measuring light 3 for scanning.

The prism 2 can be in the shape of a cone, a hemisphere, or the like.

The metal thin film and upper electrode 7 is not limited as long as it can cause surface plasmon resonance. For example, the metal thin film and upper electrode 7 can be composed of a metal thin film made of platinum, gold, or the like, preferably a gold metal thin film (e.g., manufactured by Nippon Denshi Reza). As the receptor 9, those described above can be used. For example, the receptor is immobilized on a metal thin film directly, or indirectly with a binding modification molecule, thereby producing the metal thin film on one side of which the receptor is immobilized.

The light receiving apparatus 4 may be an apparatus that converts the intensity of the reflected light 5 into a voltage using a CCD, an Si PIN photodiode (e.g., manufactured by Hamamatsu Photonics, K. K.), an operational amplifier (e.g., manufactured by National Semiconductor Corporation), a resistance device, and the like.

Figure 3A:
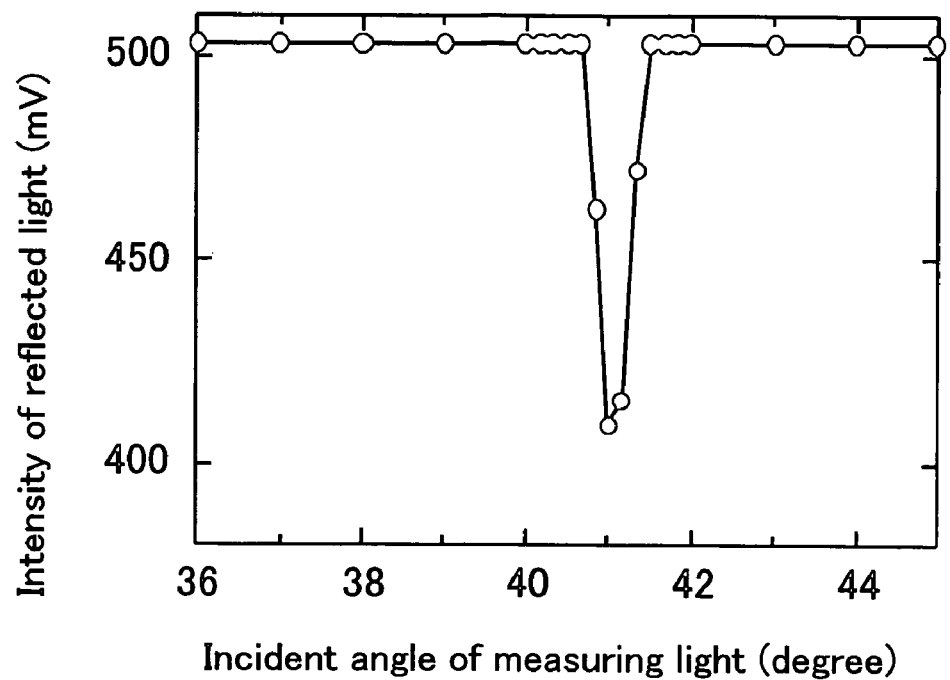
FIG. 3(a) illustrates the surface plasmon resonance curve in the absence of a receptor.
Figure 3B:
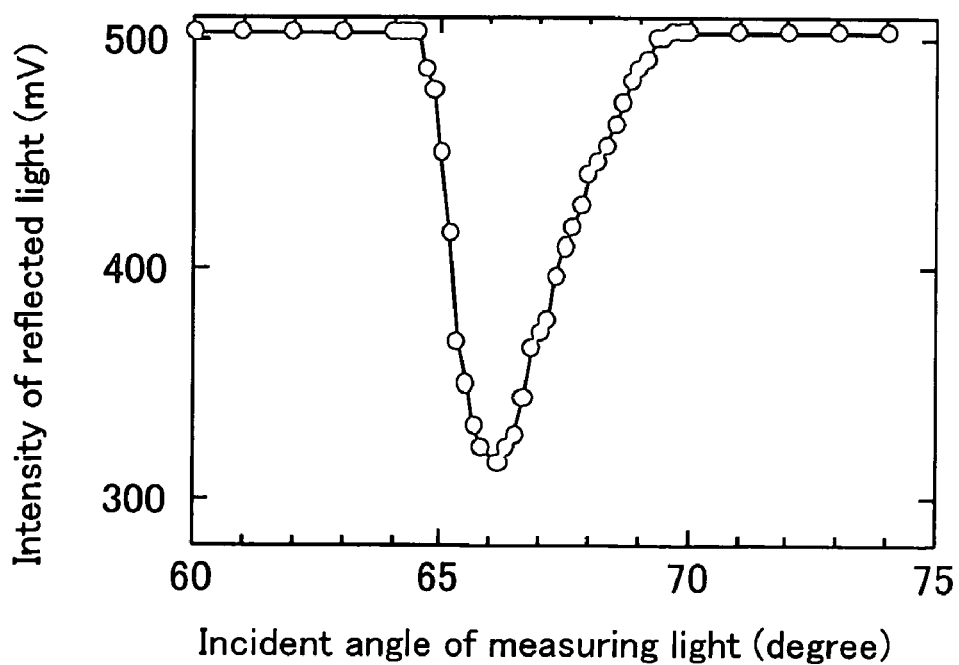
FIG. 3(b) illustrates the surface plasmon resonance curve when water is used as a receptor.

FIGS. 3(*a*) to 3(*b*) illustrate examples of a surface plasmon resonance curve measured when no receptor was provided on a metal thin film, and a surface plasmon resonance curve measured when water was provided as a receptor, in the example of the apparatus of the present invention. In each graph, the horizontal axis indicates the incident angle θ of the measuring light 3, and the vertical axis indicates the intensity of the reflected light 5. FIG. 3(*a*) illustrates the surface plasmon resonance curve in the absence of a receptor, and FIG. 3(*b*) illustrates the surface plasmon resonance curve when water is used as a receptor. Note that, in this case, external vibration is not applied during measurement. As illustrated in FIGS. 3(*a*) and 3(*b*), an angle that causes surface plasmon resonance varies depending on the presence or absence of a receptor. In other words, it is illustrated that the exemplary apparatus of the present invention can measure a change in the surface plasmon resonance angle associated with a change in the dielectric constant in the vicinity of a metal thin film.

Figure 4A:
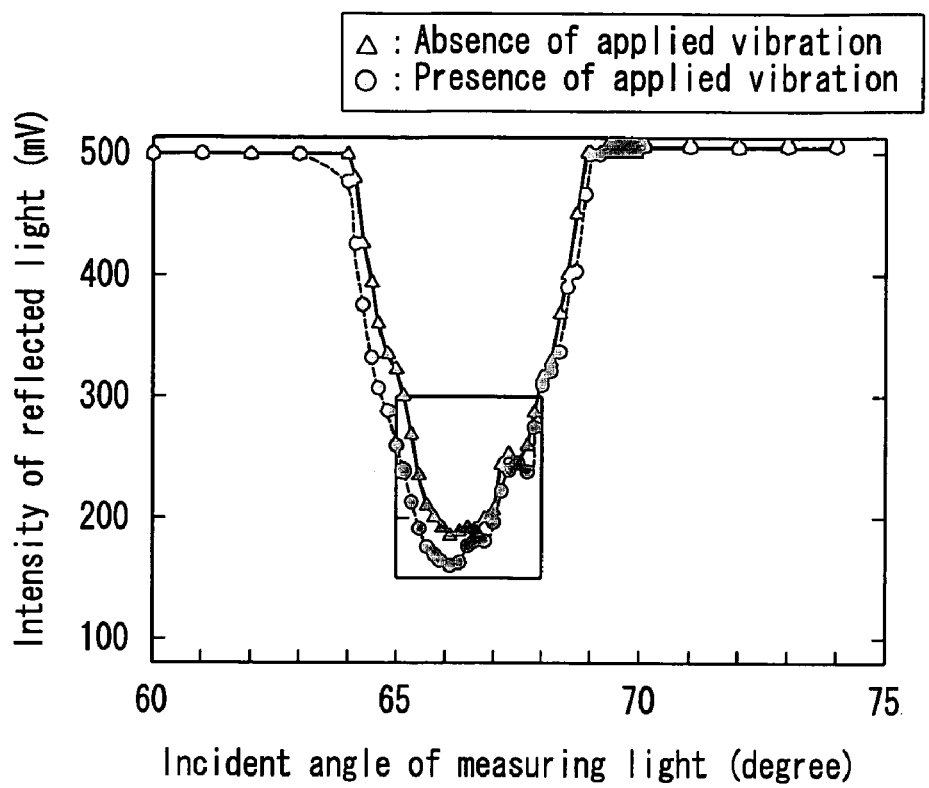
FIG. 4A illustrates exemplary surface plasmon resonance curves measured without a ligand, in the exemplary apparatus of the present invention.
Figure 4A:
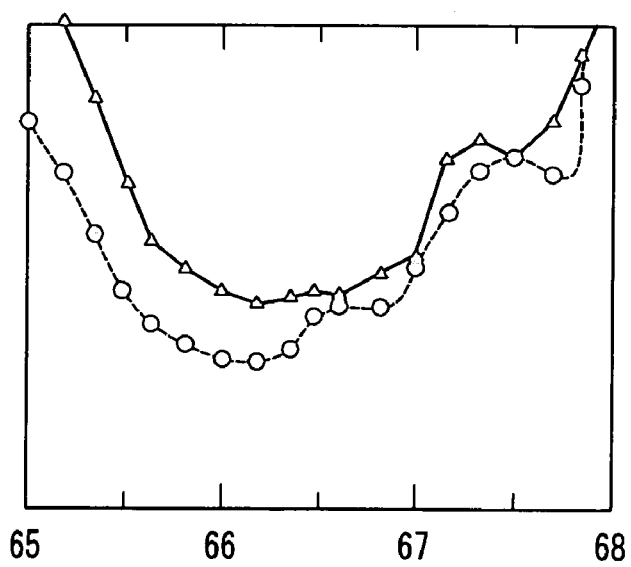

FIGS. 4A(a), 4A(b), 4B(a), and 4B(b) illustrate a surface plasmon resonance curve of a sample without a ligand and a surface plasmon resonance curve of a sample containing a ligand, in the exemplary apparatus of the present invention. In each graph, the horizontal axis indicates the incident angle θ of the measuring light 3, and the vertical axis indicates the intensity of the reflected light 5.

Figure 4B:
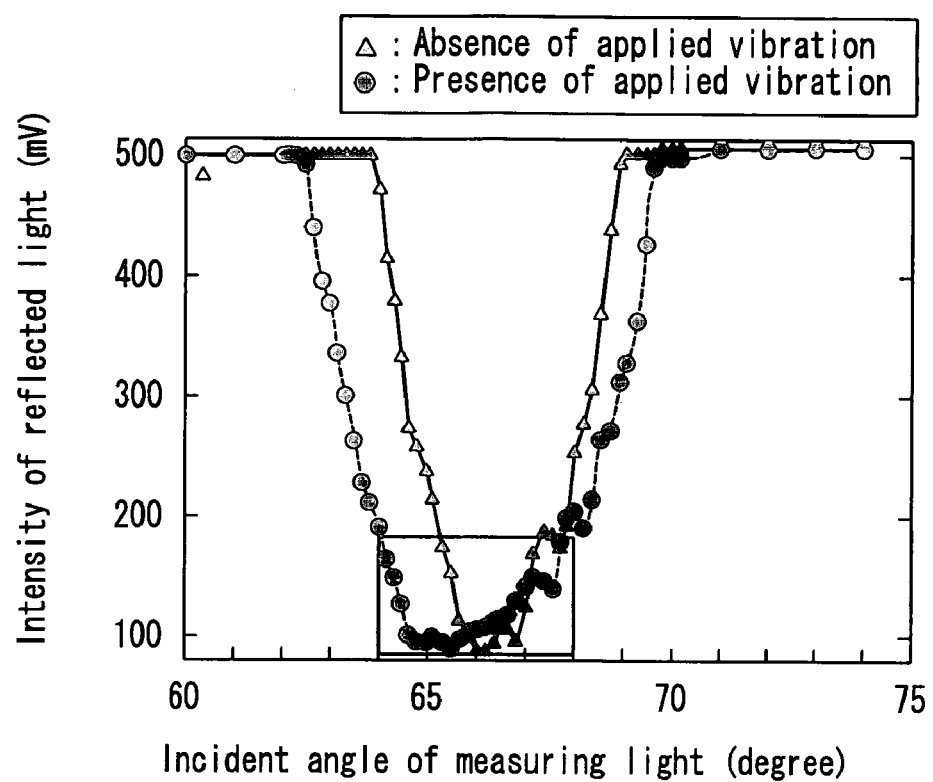
FIG. 4B illustrates exemplary surface plasmon resonance curves measured using a ligand, in the exemplary apparatus of the present invention.
Figure 4B:
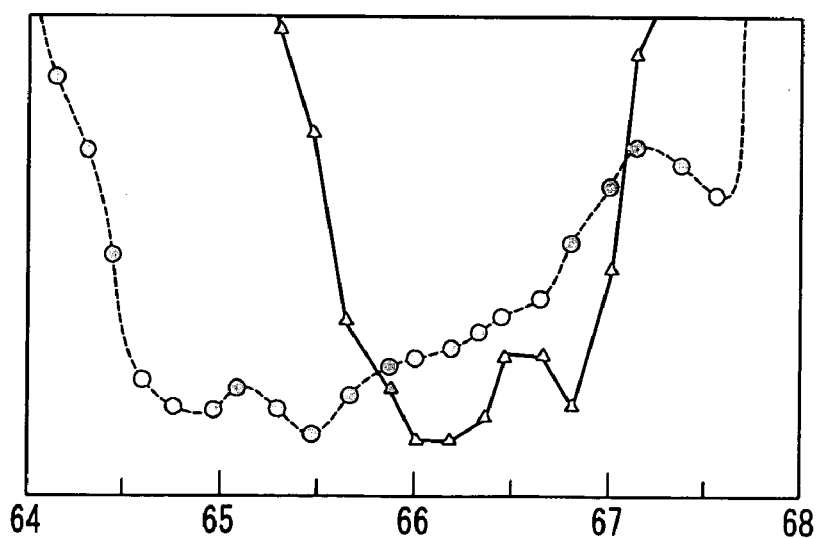

As a measuring apparatus, the exemplary apparatus of the present invention of FIG. 1 was used. As a receptor, anti-albumin bovine serum antibodies (manufactured by Sigma-Aldrich, Inc.) was used. As a sample, 1% phosphate buffer solution that was prepared by adding sodium hydroxide to phosphoric acid (manufactured by Sigma-Aldrich, Inc.) to pH 7.0, or 1% phosphate buffer solution that was prepared by adding albumin bovine serum (manufactured by Sigma-Aldrich, Inc.) and phosphoric acid (manufactured by Sigma-Aldrich, Inc.) to sodium hydroxide to 10 μg/ml and pH 7.0, respectively, was used. For both the cases when external vibration was applied and when external vibration was not applied, surface plasmon resonance curves of the samples were obtained. FIG. 4A(a) illustrates a surface plasmon resonance curve in the absence of a ligand, and FIG. 4A(b) illustrates a partially enlarged view of FIG. 4A(a). FIG. 4B(a) illustrates a surface plasmon resonance curve when albumin bovine serum was used as a ligand, and FIG. 4B(b) illustrates a partially enlarged view of FIG. 4B(a).

As illustrated in FIGS. 4A(a) and 4A(b), the surface plasmon resonance curves of the samples without a ligand are substantially the same regardless of whether or not electric field (external vibration) was applied. On the other hand, as illustrated in FIGS. 4B(a) and 4B(b), the surface plasmon resonance curve of the sample containing a ligand, measured in the presence of applied electric field, is shifted from the surface plasmon resonance curve measured in the absence of applied electric field. The present inventors infer that these results are caused by a mechanism illustrated in FIGS. 5(a) to 5(c).

Figure 5A:
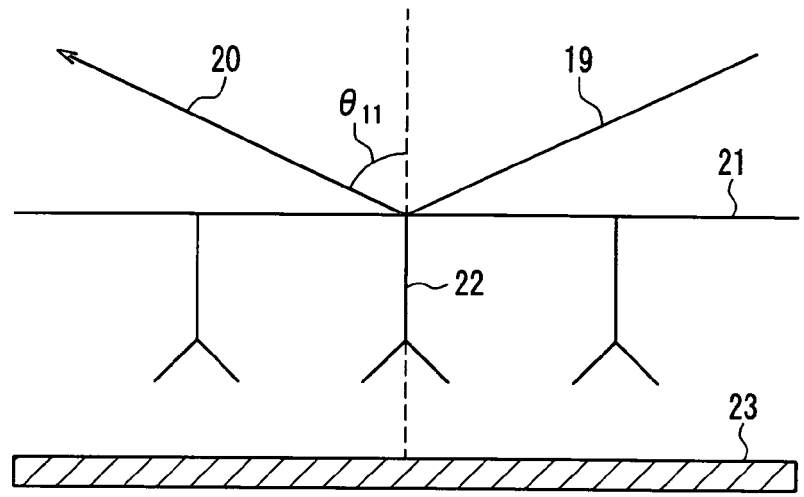
FIG. 5(a) is a schematic diagram illustrating a state when the intensity of external vibration is zero.
Figure 5B:
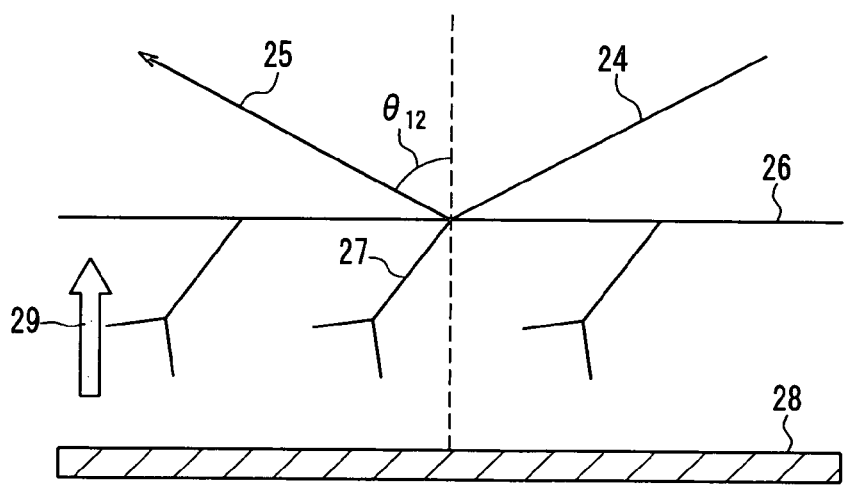
FIG. 5(b) is a schematic diagram illustrating a state when the intensity of external vibration is weak.
Figure 5C:
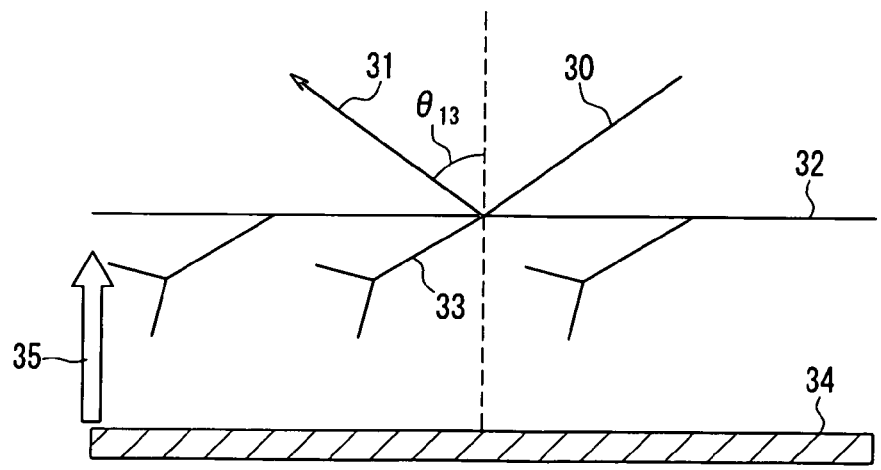
FIG. 5(c) is a schematic diagram illustrating a state when the intensity of external vibration is strong.

FIGS. 5(a) to 5(c) illustrate schematic diagrams indicating exemplary states of the vicinity of the metal thin film depending on the intensity of external vibration, in the apparatus of the present invention. FIG. 5(a) is a schematic diagram illustrating a state when the intensity of external vibration is zero, FIG. 5(b) is a schematic diagram illustrating a state when the intensity of external vibration is weak, and FIG. 5(c) is a schematic diagram illustrating a state when the intensity of external vibration is strong. In each diagram, receptors 22, 27, and 33 are immobilized on first sides of metal thin film and upper electrodes 21, 26, and 32, respectively. Measuring light beams 19, 24, and 30 are reflected on surfaces of the metal thin film and upper electrodes 21, 26, and 32, respectively, to generate reflected light dark portions 20, 25, and 31, respectively. In these cases, respective surface plasmon resonance angles are $\theta_{11}$, $\theta_{12}$, and $\theta_{13}$. In FIGS. 5(a) to 5(c), 23, 28, and 34 indicate lower electrodes, and 29 and 35 indicate external vibration.

Specifically, when the intensity of external vibration is zero, as illustrated in FIG. 5(a), when a side of the metal thin film and upper electrode 21 opposite to the side on which the receptor 22 is immobilized is irradiated with the measuring light 19, the measuring light 19 is reflected on the surface of the metal thin film and upper electrode 21, so that the reflected light dark portion 20 occurs. In this case, the receptor 22 does not follow the metal thin film and upper electrode 21, so that the surface plasmon resonance angle is $\theta_{11}$.

When the intensity of external vibration is weak, the receptor 27 slightly follows the metal thin film and upper electrode 26, so that the receptor molecules 27 gather close together on a surface of the metal thin film and upper electrode 26 as illustrated in FIG. 5(b). Therefore, the molecular density of an evanescent region on the metal thin film and upper electrode 26 is changed. Therefore, when a side of the metal thin film and upper electrode 26 opposite to the side on which the receptor 27 is immobilized is irradiated with the measuring light 24, the measuring light 24 is reflected on the surface of the metal thin film and upper electrode 26, so that the reflected light dark portion 25 occurs. The molecular density of this region is changed, so that the dielectric constant of an evanescent region also is changed, and therefore, an angle that causes surface plasmon resonance also is changed. In this case, the surface plasmon resonance angle is $\theta_{12}$.

When the intensity of external vibration is strong, the receptor 33 follows the metal thin film and upper electrode 32, so that the receptor molecules 33 gather close together on the surface of the metal thin film and upper electrode 32 as illustrated in FIG. 5(c). Therefore, an angle of the reflected light dark portion 31 that causes surface plasmon resonance is changed. The surface plasmon resonance angle is $\theta_{13}$. Thus, although surface plasmon resonance occurs at a single angle in conventional surface plasmon measuring apparatuses, the plasmon resonance occurs at a plurality of angles (not one) over time by applying external vibration. Therefore, a dark line caused by surface plasmon resonance has a width. Note that the receptor 9 is released from the vicinity of the metal thin film and upper electrode 7 by applying alternating current electric field, i.e., reversing the direction of electric field. Therefore, an angle of the reflected light dark portion 6 that causes the plasmon resonance forms a surface plasmon resonance curve similar to the one obtained in the absence of applied electric field.

Figure 6A:
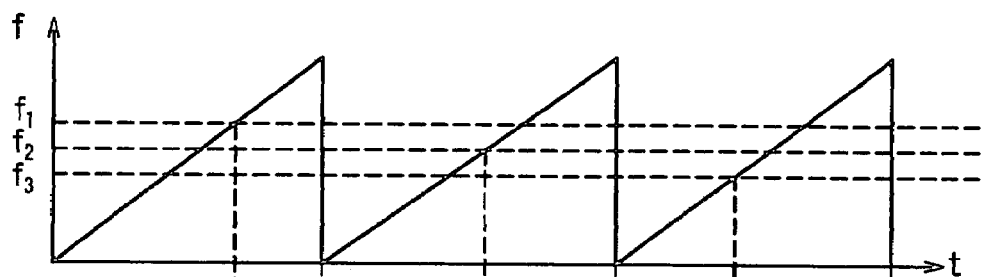
FIG. 6(a) is a diagram illustrating a temporal change in applied external vibration.
Figure 6B:
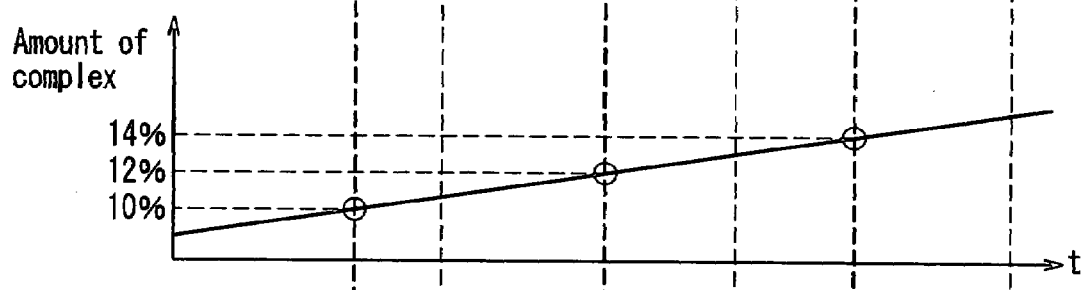
FIG. 6(b) is a diagram illustrating a temporal change in amount of a ligand-receptor complex.
Figure 6C:
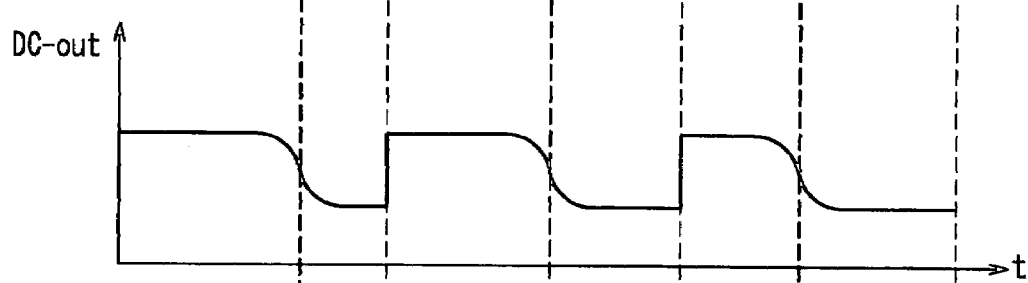
FIG. 6(c) is a diagram illustrating a sum of a phase of applied external vibration and a phase of reflected light that causes plasmon resonance.
Figure 6D:
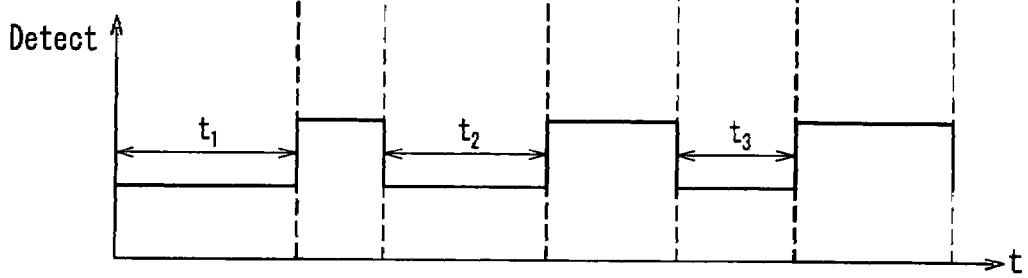
FIG. 6(d) is a diagram illustrating a digital signal that is obtained by conversion of an analog signal of FIG. 6(c) using an A/D converter.

As a specific example in which the frequency characteristics of a surface plasmon resonance angle are obtained, an example in which the phase of external vibration is compared with the phase of a signal component of external vibration included in reflected light, so that the point of inflection of the frequency characteristics of a ligand, will be described below. FIGS. 6(a) to 6(d) are diagrams for explaining the relationship between external vibration and binding of a receptor and a ligand in the present invention. FIG. 6(a) is a diagram illustrating a temporal change in swept external vibration obtained by a frequency divider. FIG. 6(b) is a diagram illustrating a temporal change in the amount of a ligand-receptor complex on a surface of a metal thin film and upper electrode. FIG. 6(c) is a diagram illustrating a sum of the phase of applied external vibration and the phase of reflected light that causes plasmon resonance, and a temporal change in an output of a detector. FIG. 6(d) is a diagram illustrating a digital signal that is obtained by conversion of an analog signal of FIG. 6(c) using an A/D converter.

As illustrated in FIG. 6(c), a temporal change in the sum of the phase of applied external vibration and the phase of reflected light that causes surface plasmon resonance is measured. A point of inflection of a curve obtained in this case is a point of inflection of frequency characteristics. For example, as the binding rate is increased to 10%, 12%, and 14%, the frequency at the point of inflection is decreased to f1, f2, and f3. Therefore, by measuring a temporal change in the point of inflection of the frequency characteristics, the degree of progress of binding of a ligand and a receptor can be measured.

The present inventors infer that the results are caused by the following mechanism. When the external vibration 13 is applied to the receptor 9 immobilized on the metal thin film and upper electrode 7, the receptor 9 tries to follow the external vibration. In a low frequency region, the receptor 9 can follow the phase of the external vibration 13 without delay, and the dielectric constant of an evanescent region is changed, so that an angle that causes surface plasmon resonance has a width. As the frequency of the external vibration is further increased, the receptor 9 follows the phase of the external vibration 13 with the delay gradually increased, and eventually cannot follow the phase of the external vibration 13. When the receptor 9 does not follow the phase of the external vibration 13, the dielectric constant of the evanescent region on the metal thin film and upper electrode 7 becomes constant, so that there is only a single angle that causes surface plasmon resonance. In other words, in the apparatus of FIG. 1, at a time when delay occurs in the following, there occurs a deviation between the phase of the external vibration 13 and the phase of the reflected light 5 generated by surface plasmon resonance, so that the amplitude of a combined wave of the phase of the external vibration 13 and the phase of the reflected light 5 that causes the plasmon resonance decreases. The point of inflection of the frequency characteristics corresponds to a time at which delay occurs in the following. As the amount of a ligand-receptor complex increases, the mass exposed to external vibration increases, so that a frequency (a frequency at the point of inflection) that does not follow is reduced (see FIGS. 6(a) and 6(b)).

By converting an analog signal of the amplitude of the output combined wave into a digital signal using the A/D converter 18 and detecting the digital signal, it is possible to obtain a time until the point of inflection of the frequency characteristics. Based on times t1, t2, and t3 until the point of inflection, the frequency characteristics can be used to detect the amount of a ligand binding to the receptor 9, which conventionally is detected based on an angle that causes plasmon resonance (see FIG. 6(d)).

Although the apparatus that uses electrical vibration has been heretofore described, a similar principle can be applied to an apparatus that uses magnetic vibration or mechanical vibration.

Second Embodiment

Figure 7:
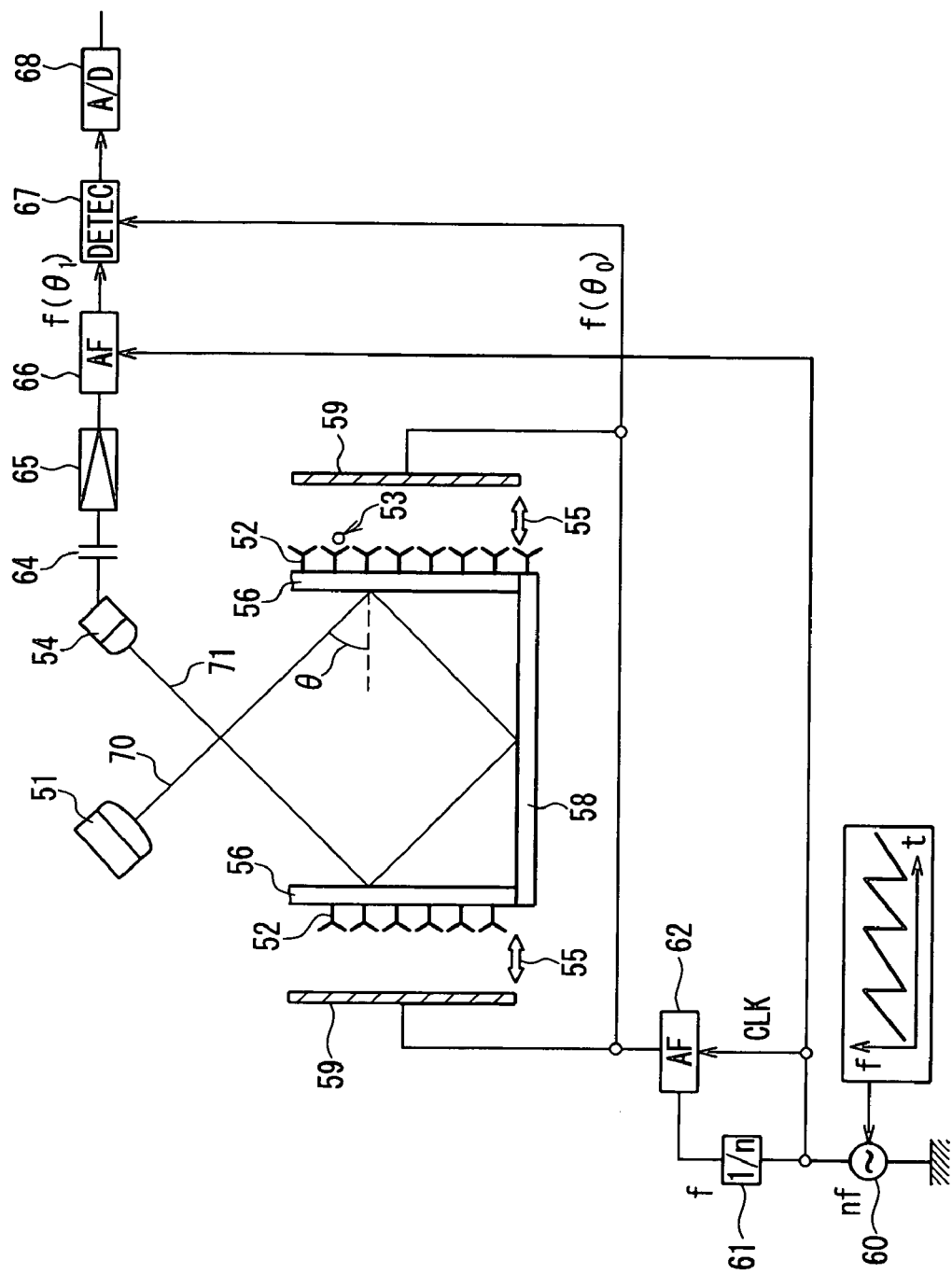
FIG. 7 is a schematic diagram illustrating another exemplary apparatus of the present invention.

In a second embodiment, another preferable embodiment of the apparatus of the present invention will be described. In FIG. 7, 51 indicates a light source. 52 indicates a receptor immobilized on a metal film and upper electrode. 53 indicates a ligand. 54 indicates a light receiving apparatus. 56 indicates a metal thin film and electrode. 58 indicates a reflector. 59 indicates an electrode. 60 indicates an alternating current source. 61 indicates a frequency divider that divides a frequency of the alternating current source 60. 62 and 66 each indicate an active filter that passes a specific frequency. 55 indicates an external vibration. 64 indicates a capacitor. 65 indicates an amplifier. 67 indicates a detector that compares a phase ($\theta_0$) of external vibration and a phase ($\theta_1$) of a signal component of external vibration included in reflected light. 68 indicates an A/D converter that converts an analog signal obtained by the detector 67 into a digital signal. 70 indicates measuring light and 71 indicates reflected light.

The exemplary apparatus of the present invention of FIG. 7 is the same as the exemplary apparatus of the present invention of FIG. 1, except that the metal thin film and electrode 56 is provided in place of the metal thin film and upper electrode 7 and the electrode 59 is provided in place of the lower electrode 8. Further, the measuring light 70 is reflected on a surface of the metal thin film and electrode 56 a plurality of times by means of the reflector 58. The light source 51 and the light receiving apparatus 54 are arranged so that the reflected light 71 is received by the light receiving apparatus 54. With such an arrangement, surface plasmon resonance is generated a plurality of times in the apparatus of the present invention. As a result, the amplitude of the surface plasmon resonance angle is amplified, thereby making it possible to achieve high-sensitivity measurement. In addition, even when the molecular weight of a receptor or a ligand is low, and therefore, the amplitude of a surface plasmon resonance angle is minute, the apparatus can amplify the amplitude of the surface plasmon resonance angle, resulting in high-sensitivity measurement.

INDUSTRIAL APPLICABILITY

As described above, the analyzing method and apparatus of the present invention measure the frequency characteristics of a surface plasmon resonance angle with respect to external vibration, which makes it possible to perform high-precision analysis without being affected by vibration and optical design. Therefore, the analyzing method and apparatus of the present invention are useful for analysis of a ligand in a sample, and are useful in the fields of, for example, biology, medicine, pharmacology, agriculture, and the like.

The invention claimed is:

1. A method for analyzing a ligand in a sample, comprising the steps of:
    causing a sample containing a ligand and a metal thin film to contact each other, wherein a receptor that can bind specifically to a ligand is immobilized on one side of the metal thin film, an optical prism is provided on an opposite side of the metal thin film, and the metal thin film can cause surface plasmon resonance, so that the ligand in the sample binds to the receptor;
    irradiating the side of the metal thin film opposite to the side on which the receptor is immobilized with measuring light using irradiating means for irradiating with measuring light;
    receiving reflected light of the measuring light reflected on the side of the metal thin film using light receiving means for receiving reflected light of the measuring light; and
    detecting a change in a surface plasmon resonance angle caused by a change in a dielectric constant of a vicinity of the metal thin film, based on the reflected light, using analyzing means for analyzing a ligand binding to the receptor;
    further comprising applying external vibration to the side of the metal thin film on which the receptor is immobilized, using applying means for applying external vibration to a region in which the receptor is immobilized, while irradiating the metal thin film with the measuring light using the irradiating means; and
    obtaining frequency characteristics of a surface plasmon resonance angle with respect to external vibration using the analyzing means, and based on the frequency characteristics, analyzing a ligand in the sample binding to the receptor, and wherein the analyzing means further includes comparing means for comparing a phase of the external vibration with a phase of a signal component of the external vibration included in the reflected light, and the step of obtaining the frequency characteristics compares the phase of the external vibration with the phase of the signal component of the external vibration included in the reflected light, using the comparing means, to detect a point of inflection of the frequency characteristics.

2. The method according to claim 1, wherein at least one of a receptor and a ligand is charged.

3. The method according to claim 1, wherein the applying means is means for applying at least one of electrical vibration, magnetic vibration, and mechanical vibration.

4. The method according to claim 1, wherein the applying means is means for applying at least electrical vibration, and the analyzing means further includes analyzing a physical property of the ligand from the reflected light.

5. The method according to claim 1, wherein an amount of a ligand in the sample binding to the receptor is analyzed.

6. The method according to claim 1, further comprising: detecting a degree of binding of the receptor and the ligand by measuring temporal change in the point of inflection of the frequency characteristics using the measuring means for measuring a temporal change in the point of inflection of the frequency characteristics, wherein the analyzing means further includes comparing means for comparing a phase of the external vibration with a phase of a signal component of the external vibration included in the reflected light, and the step of obtaining the frequency characteristics compares the phase of the external vibration with the phase of the signal component of the external vibration included in the reflected light, using the comparing means, to detect a point of inflection of the frequency characteristics.

7. The method according to claim 1, further comprising: causing the reflected light of the measuring light reflected on the side of the metal thin film on which the receptor is immobilized, using optical means for causing the reflected light of the measuring light reflected on the side of the metal thin film on which the receptor is immobilized, to impinge on the side further a plurality of times, wherein the reflected light of the measuring light received by the light receiving means is the reflected light of the measuring light reflected a plurality of times on the side of the metal thin film using the optical means.

8. The method according to claim 1, wherein a combination of a receptor and a ligand is an antigen and an antibody, an antibody and an antigen, a hormone and a hormone receptor, a hormone receptor and a hormone, a polynucleotide and a polynucleotide receptor, a polynucleotide receptor and a polynucleotide, an enzyme inhibitor and an enzyme, an enzyme and an enzyme inhibitor, an enzyme substrate and an enzyme, or an enzyme and an enzyme substrate.

9. An apparatus for analyzing a ligand in a sample, comprising:

a metal thin film, wherein a receptor that can bind specifically to a ligand is immobilized on one side of the metal thin film, an optical prism is provided on an opposite side of the metal thin film, and the metal thin film can cause surface plasmon resonance;

irradiating means for irradiating with measuring light;

light receiving means for receiving reflected light of the measuring light reflected on the side of the metal thin film;

analyzing means for analyzing a ligand binding to the receptor;

wherein the apparatus further comprises applying means that can apply external vibration to the side of the metal thin film on which the receptor is immobilized, and a side of the metal thin film opposite to the side on which the receptor is immobilized, can be irradiated with measuring light using the irradiating means while applying external vibration using the applying means, and the analyzing means can detect a change in a surface plasmon resonance angle from the reflected light and obtain frequency characteristics of a surface plasmon resonance angle with respect to external vibration, and based on the frequency characteristics, analyze a ligand in the sample binding to the receptor wherein the analyzing means further comprises comparing means for comparing a phase of the external vibration with a phase of a signal component of the external vibration included in the reflected light so that a point of inflection of the frequency characteristics can be detected.

10. The apparatus according to claim 9, wherein at least one of a receptor and a ligand is charged.

11. The apparatus according to claim 9, wherein the applying means is means for applying at least one of electrical vibration, magnetic vibration, and mechanical vibration.

12. The apparatus according to claim 9, wherein the applying means is means for applying at least electrical vibration, and the analyzing means further can analyze a physical property of the ligand from the reflected light.

13. The apparatus according to claim 9, wherein an amount of a ligand in the sample binding to the receptor is analyzed.

14. The apparatus according to claim 9, further comprising measuring means for measuring a temporal change in the point of inflection of the frequency characteristics so that a degree of binding of the receptor and the ligand can be detected.

15. The apparatus according to claim 9, further comprising optical means that can cause the reflected light of the measuring light reflected on the side of the metal thin film on which the receptor is immobilized, to impinge on the side further a plurality of times, wherein the reflected light of the measuring light received by the light receiving means is the reflected light of the measuring light reflected a plurality of times on the side of the metal thin film using the optical means.

16. The apparatus according to claim 9, wherein a combination of a receptor and a ligand is an antigen and an antibody, an antibody and an antigen, a hormone and a hormone receptor, a hormone receptor and a hormone, a polynucleotide and a polynucleotide receptor, a polynucleotide receptor and a polynucleotide, an enzyme inhibitor and an enzyme, an enzyme and an enzyme inhibitor, an enzyme substrate and an enzyme, or an enzyme and an enzyme substrate.

* * * * *